Figure 1:
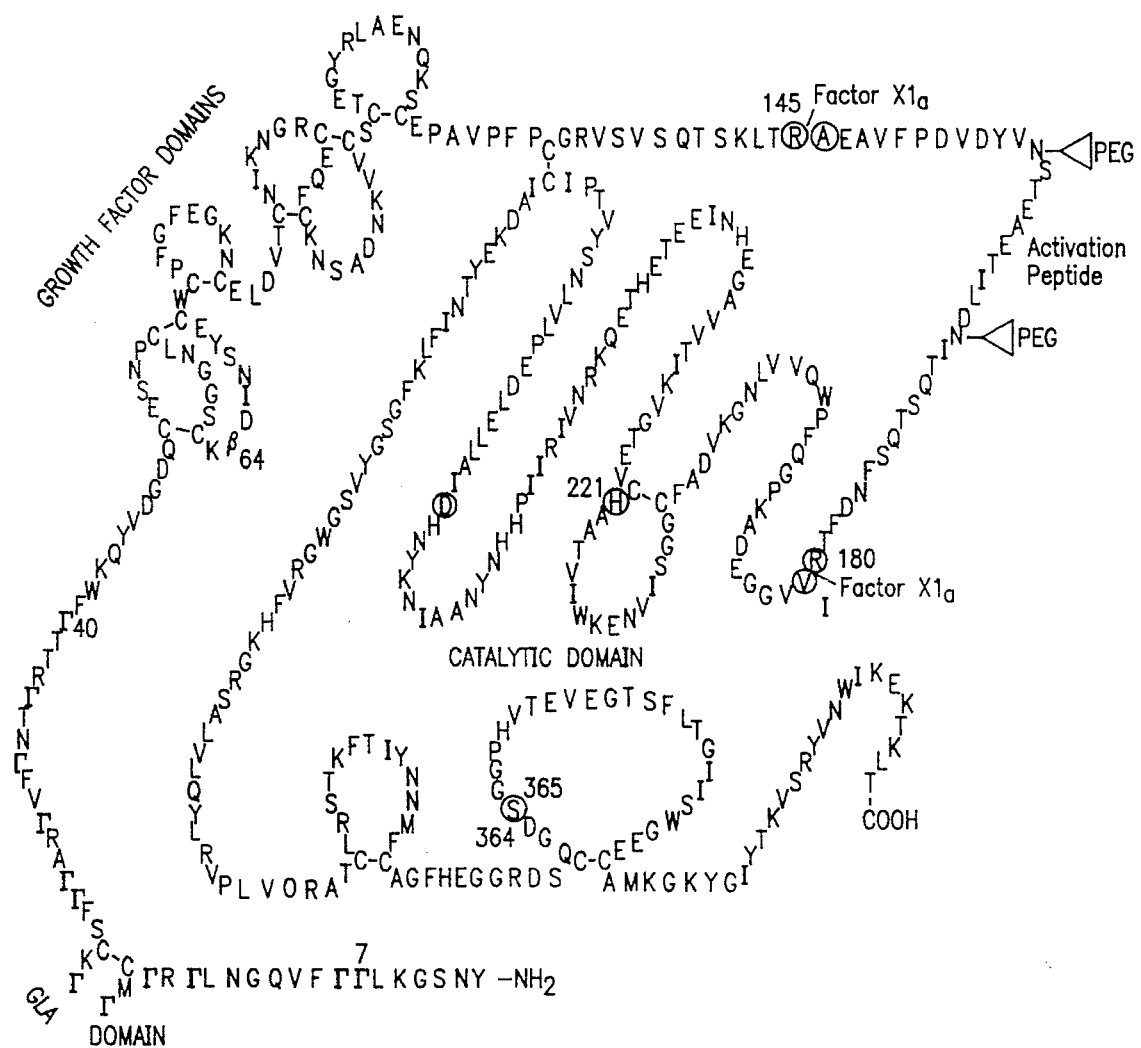

United States Patent [19]

Hallahan et al.

[11] Patent Number: 5,621,039

[45] Date of Patent: Apr. 15, 1997

[54] FACTOR IX- POLYMERIC CONJUGATES

[76] Inventors: Terrence W. Hallahan, 82 Hazelwood Ave., Metuchen, N.J. 08840; Carl W. Gilbert, 26 Hampton Ct., Basking Ridge, N.J. 07920

[21] Appl. No.: 73,531

[22] Filed: Jun. 8, 1993

[51] Int. Cl.$^6$ ..................................... A61K 38/00
[52] U.S. Cl. .......................... 525/54.1; 525/54.2; 530/381
[58] Field of Search ..................... 530/381, 815, 530/829, 810, 812, 813, 816; 435/219; 525/54.1, 54.2, 54.24

[56] References Cited

U.S. PATENT DOCUMENTS

| | | | |
|---|---|---|---|
| 3,717,708 | 2/1973 | Wada et al. | 530/384 |
| 4,970,300 | 11/1990 | Fulton et al. | 530/383 |
| 5,153,265 | 10/1992 | Shadle et al. | 524/54.1 |

OTHER PUBLICATIONS

Busby et al. Expression of Active Human Factor IX in Transfected Cells, Nature, vol. 316, Jul., 1985, pp 271–273.

Kaufman et al., Expression, Purification and Characterization of Recombinant γ-Carboxylated Factor IX Synthesized in Chinese Hamster Ovary Cells, The Journal of Biological Chemistry, vol. 261, No. 21, Jul., 1986, pp 9622–9628.

Hertzberg et al., Construction, Expression, and Characterization of a Chimera of Factor IX and Factor X, The Journal of Biological Chemistry, vol. 267, No. 21, Jul., 1992 pp. 14759–14766.

*Primary Examiner*—Jeffrey C. Mullis
*Attorney, Agent, or Firm*—Galgano & Burke

[57] ABSTRACT

Conjugates containing a substance with coagulant activity, such as recombinant Factor IX, non-antigenic polymers, such as poly(ethylene glycol), are disclosed. Also disclosed are methods of forming the novel conjugates of this invention.

9 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 415 Amino Acids
        ( B ) TYPE: Amino Acid
        ( C ) STRANDEDNESS: Single
        ( D ) TOPOLOGY: Unknown to applicant ( i i ) MOLECULE TYPE: -

( i i i ) HYPOTHETICAL: -

( i v ) ANTI-SENSE: -

( v i ) ORIGINAL SOURCE:
        ( A ) ORGANISM: -
        ( C ) INDIVIDUAL ISOLATE: -
        ( G ) CELL TYPE: -

( v i i ) IMMEDIATE SOURCE:
        ( A ) LIBRARY:
        ( B ) CLONE:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( K ) RELEVANT RESIDUES IN SEQ ID NO: 1: FROM 1 TO 415.

( x i ) SEQUENCE DESCRIPTION: SEQ ID NO: 1 :

```
Tyr Asn Ser Gly Lys Leu Glu Glu Phe Val Glu Gly Asn Leu Glu Arg
 1               5                  10                  15

Glu Cys Met Glu Glu Lys Cys Ser Phe Glu Glu Ala Arg Glu Val Phe
            20                  25                  30

Glu Asn Thr Glu Lys Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140
```

```
Arg Ala Glu Ala Val Phe Pro Asp Val Asp Tyr Val Asn Pro Thr Glu
145                 150                 155                 160

Ala Glu Thr Ile Leu Asp Asn Ile Thr Gln Gly Thr Glu Ser Phe Asn
            165                 170                     175

Asp Phe Thr Arg Val Val Gly Gly Glu Asp Ala Lys Pro Gly Gln Phe
            180             185                     190

Pro Trp Gln Val Val Leu Asn Gly Lys Val Asp Ala Phe Cys Gly Gly
        195             200             205

Ser Ile Val Asn Glu Lys Trp Ile Val Thr Ala Ala His Cys Val Glu
    210             215             220

Thr Gly Val Lys Ile Thr Val Val Ala Gly Glu His Asn Ile Glu Glu
225             230                 235                 240

Thr Glu His Thr Glu Gln Lys Arg Asn Val Ile Arg Ile Ile Pro His
            245                 250                 255

His Asn Tyr Asn Ala Ala Ile Asn Lys Tyr Asn His Asp Ile Ala Leu
            260             265             270

Leu Glu Leu Asp Glu Pro Leu Val Leu Asn Ser Tyr Val Thr Pro Ile
        275             280             285

Cys Ile Ala Asp Lys Glu Tyr Thr Asn Ile Phe Leu Lys Phe Gly Ser
    290             295                 300

Gly Tyr Val Ser Gly Trp Gly Arg Val Phe His Lys Gly Arg Ser Ala
305             310                 315                 320

Leu Val Leu Glu Tyr Leu Arg Val Pro Leu Val Asp Arg Ala Thr Cys
            325             330                 335

Leu Arg Ser Thr Lys Phe Thr Ile Tyr Asn Asn Met Phe Cys Ala Gly
        340             345             350

Phe His Glu Gly Gly Arg Asp Ser Cys Gln Gly Asp Ser Gly Gly Pro
        355             360             365

His Val Thr Glu Val Glu Gly Thr Ser Phe Leu Thr Gly Ile Ile Ser
    370             375             380

Trp Gly Glu Glu Cys Ala Met Lys Gly Lys Tyr Gly Ile Tyr Thr Lys
385             390             395             400

Val Ser Arg Tyr Val Asn Trp Ile Lys Glu Lys Thr Lys Leu Thr
            405             410             415
```

FACTOR IX- POLYMERIC CONJUGATES

The present invention is directed to methods of modifying substances having Factor IX activity, such as the procoagulant glycoprotein Factor IX and, more particularly, to methods for the modification of such substances with non-antigenic polymers, such as polyethylene glycol, and the resultant conjugates.

BACKGROUND OF THE INVENTION

The process of blood clotting typically begins with trauma to a blood vessel. The damaged vessel wall initiates hemostasis by causing adherence and accumulation of platelets at the injury site and by activating plasma proteins which initiate the coagulation process. A series of proteins, including Factor IX, are activated sequentially by specific proteolytic cleavages and conformational changes leading to the deposition of insoluble fibrin which curtails the blood flow.

Blood coagulation Factor IX circulates as an inactive zymogen. It enters the coagulation cascade after activation in the presence of Factor XIa or VIIa and tissue factor. The activated Factor IX (IXa) in turn activates Factor X in the presence of Factor VIIIa, phospholipids and calcium.

Hemophilia is a bleeding disorder caused by the lack of an essential blood factor. Hemophilia A (classic hemophilia) is the most common and is caused by a genetic deficiency or abnormality of Factor VIII. Hemophilia B is caused by a deficiency or abnormality of Factor IX. The genetic deficiency of Factor IX results in hemophilia B. It has been estimated that about 3000 patients in the U.S. alone suffer from hemophilia B.

Hemophilia is a heterogeneous disorder. Mutant blood Factor IX proteins can have clotting activities that vary from near normal to severely deficient. The clinical features of hemophilia A and B are identical. Less than 1% clotting factor activity is defined as severe hemophilia, and is accompanied by spontaneous bleeding in the muscles and larger joints. Repeated bleeding in joints causes arthropathy or hemarthroses which is a major chronic complication. Hemarthroses are worsened by muscle atrophy due to muscle bleedings. Often, repeated hemarthroses result in eventual deformity and crippling. In mild hemophilia (5–40% FVIII or FIX activity), bleeding does not occur except after trauma. Moderately severe hemophilia (1–5% FVIII or FIX activity) has clinical features between the severe and mild hemophilia.

Conventional treatment of hemophilia B consists of replacement of the deficient Factor IX from pooled donor plasma including fresh, frozen plasma or Factor IX concentrates. Pooled donor preparations, however, have been associated with the transmission of viral diseases such as hepatitis (eg. B, delta, non A non B) and HIV. This is in spite of increased purification techniques to reduce the virus load. It has been estimated that 50% of hemophilia patients are either hepatitis positive or HIV positive. These viral infections are now the major cause of morbidity and mortality in patients with hemophilia.

Further disadvantages of pooled donor plasma include the cost and availability of the purified blood factors. With increased purification steps, the cost of blood factor therapy has increased. Availability of the blood factors is also a concern. Theoretically, these factors should be administered prophylactically in many cases to avoid the sequelae of uncontrolled bleeding such as the development of joint disorders. However, cost, availability and the pharmacokinetics make an effective prophylactic therapy unfeasible.

With the advent of DNA technology, researchers have now cloned and are testing a number of recombinant blood factors, including Factor IX in patients with hemophilia. While recombinant technology may overcome the problems of vital contamination and availability, it does not affect the pharmacokinetics of the factors nor the formation of inhibitors (antibodies) in patients. It is estimated that 2–3% of all patients with hemophilia B will develop IgG antibodies that will nullify the value of replacement therapy. Inhibitor development occurs primarily in patients with severe hemophilia although antibodies to Factor IX in mild hemophilia have been reported. Approximately 5–15% of patients with severe hemophilia have antibodies to Factor VIII or IX. It has been estimated that the actual risk of developing neutralizing antibodies by age 20 is as high as 15–24%. Joint bleedings often cannot be controlled and adequately treated and many of these patients are severely handicapped.

To overcome the neutralizing effect of the antibodies, physicians can be forced to increase the dosage to the factor. However, there is often a decreased response to the replacement therapy despite increases in dosage. Care in administering the factors as well as the administration of steroids and other immunosuppressive agents such as azathioprine, cyclophosphamide and high-dose gammaglobulin G is often required to prevent or limit the development of antibodies and hypersensitivity reactions. Antibody depletion through plasmapheresis has been used to decrease the inhibitor titers in circulation. However, such immunosuppressive techniques have been only partially successful and raise the risk that the patient will be more vulnerable to opportunistic infections, e.g. HIV or hepatitis.

In light of the complications and risks inherent in the conventional treatment of hemophilia B, it is desirable to provide compositions having Factor IX activity which are less likely to cause the formation of inhibitor antibodies. In light of the high costs of Factor IX, it is also highly desirable to increase the in vivo circulating life of Factor IX activity.

SUMMARY OF THE INVENTION

The various embodiments of the present invention provide conjugates having Factor IX activity with reduced propensities to develop problems relating to immunogenecity and antigenicity. In addition, there are also provided methods for the modification of substances such as glycopolypeptides or fractions thereof having Factor IX activity with non-antigenic polymeric materials, such as polyethylene glycol (PEG). The Factor IX substance included in the conjugates is preferably one which has been formed using recombinant technology. The Factor IX substance may also be derived from human or animal plasma sources, such as bovine or porcine plasma. Transgenic sources are also contemplated. As used herein, the term "Factor IX substance or fraction" means any substance which demonstrates the ability in vivo to function as mammalian Factor IX, i.e. activate Factor X and continue the intrinsic clotting cascade. The Factor IX fraction can also comprise other proteins and reagents, as well as other serum proteins including albumin, fibrin, fibrinogen, etc., which do not interfere with in vivo activity.

An advantage of one preferred embodiment of the present invention lies in the fact that the substantially non-antigenic material is attached to the activation region of the Factor IX. Since Factor IX is activated by the proteolytic removal of the activation region, the substantially non-antigenic polymer is removed from the Factor IX upon activation and therefore does not interfere with the normal functioning of the activated protein. Thus the benefits normally achieved with conjugation of a non-antigenic polymer can be obtained producing a long-circulating procoagulant without interfering with the structure or physiologic activity of the activated Factor IX.

According to one embodiment of the present invention, substances containing Factor IX activity are reacted with a substance capable of oxidizing vicinal diols of carbohydrate moieties in the activation region to form aldehydes. One or more substantially non-antigenic polymers can then be covalently attached to the oxidized carbohydrate moieties. The polymers are preferably activated or functionalized to include a terminal hydrazine group such as, for example, an acyl hydrazine. These reactions are performed under conditions sufficient to effect conjugation while maintaining at least a portion of the Factor IX activity. The resulting Factor IX may then be stabilized in a manner known to those of ordinary skill in the art with human serum albumin (HSA) or glycine, sterile filtered and, if desired, lyophilized. This method has been found to provide a long-circulating Factor IX-acting conjugate which is less susceptible to antibody inhibitors and retains an effective amount of the unmodified substance's original activity.

These and other embodiments of the present invention are described in detail below.

BRIEF DESCRIPTION OF THE DRAWINGS

FIG. 1 is a schematic representation of Factor IX showing the amino acid sequence, structure and various domains.

DETAILED DESCRIPTION

The various embodiments of the present invention advantageously provide methods for modifying substances having Factor IX activity with substantially non-antigenic polymeric substances Under relatively mild conditions, for example at a pH of about 5–7 with about 5.5–6.5 preferable and at temperatures which do not exceed 37° C., and are preferably in the range of from 10°–25° C. Those skilled in the art will appreciate, for example, that human Factor IX is a relatively large and sensitive glycoprotein. The present invention provides methods for modifying such glycoproteins without subjecting them to conditions which would eliminate their activity.

The substantially non-antigenic polymer substances included in the conjugates are preferably poly(alkylene oxides). Within this group of substances are alpha-substituted polyalkylene oxide derivatives such as methoxypolyethylene glycols or other suitable alkyl-substituted derivatives such as those containing $C_1$–$C_4$ alkyl groups. It is preferred, however, that the non-antigenic material be a monomethyl-substituted PEG homopolymer. Alternative polymers such as other polyethylene glycol homopolymers, polypropylene glycol homopolymers, other alkyl-polyethylene oxides, bis-polyethylene oxides and co-polymers or block co-polymers of poly(alkylene oxides) are also useful. In those aspects of the invention where PEG-based polymers are used, it is preferred that they have molecular weights of from about 200 to about 10,000. Molecular weights of about 2,000 to 7,000 are preferred and molecular weights of about 5,000 are particularly preferred. Alternatively, other non-antigenic polymers such as dextran, polyvinyl pyrrolidone, starches, complex carbohydrates and other substantially non-antigenic compounds known in the art may also be linked to a compound exhibiting Factor IX activity in vivo by covalent or non-covalent modification.

Human Factor IX is a single chain glycoprotein of 57,000 Daltons. Structurally, it can be considered as having four essential domains (FIG. 1). The Gla or gamma carboxyglutamate rich domain, the EGF-like regions, the activation peptide and the active site. The Gla domain encompasses the first 46 residues including 12 gamma carboxy-glutamate residues. Residues 47–127 form the EGF-like region. The activation region encompasses residues 128–195 and the two cleavage sites for Factor XIa are Arg144–Ala146 and Arg180–Val181. The activation peptide, which is unbound upon activation, contains 35 amino acid residues and two Asp-linked carbohydrate side chains. The final 220 residues form the heavy chain of activate Factor IX and contain the enzyme active site.

As stated above, one particularly preferred embodiment includes recombinantly prepared substances having Factor IX activity in vivo. A non-limiting list of suitable recombinant glycoproteins include those described in J. Biological Chemistry, Vol. 261, No. 21, pp. 9622–9628, (1986); J. Biological Chemistry, Vol. 267, No. 21, pp. 14759–14766 (1992); and Nature, Vol. 316, pp. 271–273 (1985), wherein it is reported: As a first step towards an alternative source of pure human factor IX; we report here on the use of recombinant DNA techniques to produce biologically active factor IX in cultured mammalian cells. Stable cell lines were produced by co-transfecting a baby hamster kidney (BHK) cell line with a plasmid containing a gene for factor IX and a plasmid containing a selectable marker. Protein secreted by these cell lines reduces the clotting time of plasms from factor IX-deficient patients. We present additional evidence that this protein is authentic human factor IX.

To express factor IX in cultured cells, we used a complementary DNA containing 138 base pairs (bp) that encode the 46-amino-acid leader, 1,248 bp that encode the 415 amino-acid mature protein and 48 bp of 3' noncoding DNA sequence. As described in FIG. 1 legend, this cDNA was inserted into a plasmid containing the adenovirns-2 major late promotor, a set of RNA splice sites and the simian virus 40 (SV40) polyadenylation signal. BHK cells were co-transfected with the factor IX plasmid (FIX/pD2) and pKO-neo, a plasmid containing the gene for resistance to the antibiotic G418 (ref. 6). G418-resistant colonies were isolated and screened for the presence of factor IX activity secreted into the media; ~50% of the resistant colonies analysed secreted detectable factor IX activity. In subsequent analyses of a representative clone (IX-F), the supernatant media and the cell pellets of clone IX-F were assayed for the amounts of biologically active factor IX and factor IX polypeptide. The assay for biological activity was based on the ability of the sample to reduce the blood clotting time of plasma from factor IX-deficient patients and the amount of factor IX polypeptide was determined by an enzyme-linked immunosorbent assay (ELISA) using an affinity-purified polyclonal rabbit antibody to factor IX. The cells were grown for different lengths of time, and the media and cells collected for analysis. Most of the factor IX polypeptide (70–80%) was secreted into the media, and ~50% of the secreted protein was biologically active. No biological activity was detected in the cellular extracts despite the presence of factor IX polypeptide. Extracts of BHK cells had no inhibitory effect on the clotting assay.

Construction of Factor IX Expression Plasmid p91023-IX

To replace the weaker Factor IX promoter with a stronger promoter for efficient expression in mammalian cells, the Factor IX coding region was excised separate from its promotor and inserted into a derivative of the mammalian expression vector p91023(B) (24) by the following procedure. A 3.5-kb XbaI fragment containing the Factor IX minigene was purified and digested with exonuclease III for the time required to degrade the 5' noncoding sequence. The DNA was then treated with S1 endonuclease and Klanow fragment of polymerase 1 and blum-end ligated to a synthetic PstI adapter

5'-CTAGAGGCCTCTGCA-3'
3'-GATCTCCGGAG      -5'

The adapted DNA was cloned into an M13 mpII PstI vector. Recombinant plaques were screened with an oligonucleotide homologous to the first 17 base pairs of Factor IX coding sequence MRNA. One subclone was isolated in which the PstI adapter had ligated 19 nucleotides upstream of the initiator codon and contained the entire Factor IX coding sequence and 1030 nucleotides of 3' uptranslated sequence. The resultant plasmid was sequenced by the dideoxy chain termination method using synthetic oligonucleotide primers. The nucleotide sequence of the coding region was in complete agreement with that published by Choo et al.

A 2.5-kb fragment containing the Factor IX coding region was then isolated and inserted into the PstI site of the mammalian expression vector pQ2, in place of —interferon. The resultant Factor IX expression plasmid, designated p91023-IX, contained the Factor IX coding region in the proper orientation with respect to the adenovirus major late promoter.

Cell culture, DNA Transfection and Cell Line Selection

Growth and maintenance of the dihydrofolate reductase-deficient CHO DUKX-B11 cell line has been described. DUKX-B11 cells were transfected with a mixture of the Factor IX expression plasmid (25 µg, p91023-IX) and a dihydrofolate reductase expression plasmid (2.5 µg, pAdD26SVpA#3.28) by $CaPO_4$

5'-CTAGAGGCCTCTGCA-3'
3'-GATCTCCGGAG      -5'

The adapted DNA was cloned into an M13 mpII PstI vector. Recombinant plaques were screened with an oligonucleotide homologous to the first 17 base pairs of Factor IX coding sequence MRNA. One subclone was isolated in which the PstI adapter had ligated 19 nucleotides upstream of the initiator codon and contained the entire Factor IX coding sequence and 1030 nucleotides of 3' uptranslated sequence. The resultant plasmid was sequenced by the dideoxy chain termination method using synthetic oligonucleotide primers. The nucleotide sequence of the coding region was in complete agreement with that published by Choo et al.

A 2.5-kb fragment containing the Factor IX coding region was then isolated and inserted into the PstI site of the mammalian expression vector pQ2, in place of γ-interferon. The resultant Factor IX expression plasmid, designated p91023-IX, contained the Factor IX coding region in the proper orientation with respect to the adenovirus major late promoter.

Cell culture, DNA Transfection and Cell Line Selection

Growth and maintenance of the dihydrofolate reductase-deficient CHO DUKX-B11 cell line has been described. DUKX-B11 cells were transfected with a mixture of the Factor IX expression plasmid (25 µg, p91023-IX) and a dihydrofolate reductase expression plasmid (2.5 µg, pAdD26SVpA#3.28) by $CaPO_4$ coprecipitation. After transfection, the cells were fed with α-medium containing 10% fetal bovine serum and thymidine, adenosine, deoxyadenosine, penicillin, and streptomycin (10 µg/ml each). Two days later the cells were subcultured into α-medium with 10% dialyzed fetal bovine serum, penicillin, and streptomycin, but lacking nucleosides. Cells were fed again with the selective media after 4–5 days, and colonies appeared 10–12 days after subculturing. Initial transformants were pooled (approximately 25 transformants per pool) and grown in increasing concentrations of methotrezate starting from 0.02 µM and extending up to 200 µM methotrexate (0.02, 0.2, 0.5, 1.0, 5.0, 20, and 200 µM). The selected pool (5α3) was then cloned in 200 µM methotrexate.

Immunoaffinity Purification of Carboxylated Recombinant Factor IX

Carboxylated recombinant Factor IX was purified from the culture medium of Chinese hamster ovary cells by immunoaffinity chromatography using conformation-specific antibodies. In this strategy, antibodies are employed to bind to forms of Factor IX that can express specific antigenic determinants only in the presence of metal ions. A-γ-carboxy-and des-γ-carboxy recombinant Factor IX can not assume the metal-stabilized conformation and thus do not bind to these antibodies. Culture medium (930 ml) was concentrated at 4° C. by ultrafiltration to a volume of 420 ml using a PM30 membrane (Amicon). The crude Factor IX preparation was dialyzed three times against 10 volumes of 3 mM $CaCl_2$, 0.05M Tris-HCl. 0.5M NaCl and applied to an anti-factor IX: Ca(II)–Sepharose column (1.5×2 cm) as previously described. The column was washed exhaustively with the equilibration buffer and then eluted with 10 mM EDTA, 0.05M Tris-HCl, 0.15M NaCl.

It will be understood that in those situations where recombinant sources of Factor IX activity substances are selected, modifications such as amino acid substitutions or other mutants which do not effect or eliminate Factor IX activity are within the scope of the present invention. Moreover, in those situations where non-human Factor IX substances are included, some differences in homology are recognized. These alternatives, however, have the desired in vivo activity and the preferred activation region polymeric attachment site(s).

As stated above, covalent modification of the protein material is preferred. The modification reaction includes reacting a substance having the desired Factor IX activity with a substantially non-antigenic polymeric substance under conditions sufficient to effect conjugation while maintaining at least a portion of the Factor IX activity.

Preferably, one or more polymer chains are covalently attached to the Factor IX by reacting suitably activated non-antigenic polymers with oxidized carbohydrate moieties in the activation region. Reactive carbonyl groups can be generated on saccharide units of the carbohydrate moieties, for example, by oxidizing vicinal diols with excess sodium periodate utilizing steps understood by those of ordinary skill in the art. The reactive carbonyls can also be generated enzymatically, e.g., by use of galactose oxidase or neuraminidase and galactose oxidase. For purposes of the present invention, enzymatic oxidation is preferred.

"Suitably activated non-antigenic polymers" is understood by those of ordinary skill in the art to mean that the polymer is functionalizing to include a group capable of linking the polymer to the Factor IX substance. Preferably, the functionalized moiety is reactive with oxidized carbohydrate moieties, such as hydrazine.

Preferred hydrazine activated polymers of the present invention are acyl hydrazines having a structure corresponding to Formula I:

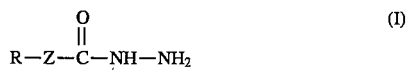

wherein R is one of the above-disclosed water-soluble non-antigenic polymers and Z is O, NH, S or a lower alkyl group containing up to ten carbon atoms. See, for example, commonly assigned PCT Int'l. Publication No. WO92/16555 which is incorporated by reference herein.

The acyl hydrazine derivative in which Z is O (mPEG-Carbazate) is prepared by reacting, for example, the methoxypolyethylene glycol-N-succinimide carbonate described in U.S. Pat. No. 5,122,614 with an excess of hydrazine in an organic solvent in which the reactants are soluble, such as methanol, methylene chloride, or toluene. The disclosure of U.S. Pat. No. 5,122,614 with respect to the preparation of methoxypolyethylene glycol-N-succinimide carbonate is hereby incorporated by reference. After the reaction is completed, the solvents and excess hydrazine are then removed utilizing conventional techniques.

The preparation of acyl hydrazine polymer derivatives is described with reference to MPEG for purposes of illustration, not limitation. Similar products would be obtained with any of the polymers suitable for use with the present invention, and it will be clear to those of ordinary skill in the art how this preparation can be adapted to the other suitable polymers.

The reaction of the acyl hydrazines of Formula I with a glycoprotein having Factor IX activity to form a hydrazone linkage is illustrated by the reaction sequence of Scheme 1. R and Z are the same as described above and $R_1$ and $R_2$ form an oxidized carbohydrate moiety on which reactive carbonyl groups have been generated:

Scheme 1

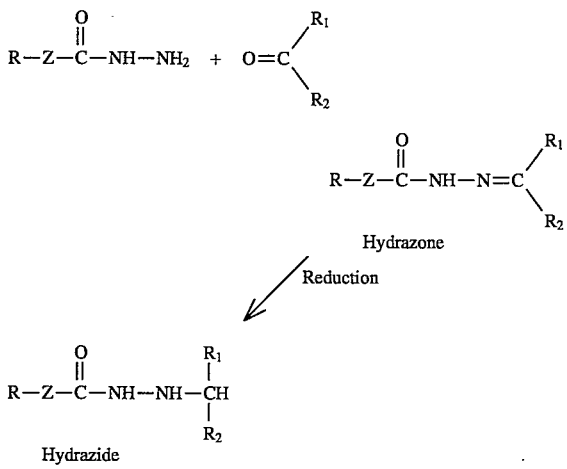

In one aspect of this embodiment, the hydrazone can be reduced to the more stable alkyl hydrazide by reacting the hydrazone with, for example, $NaBH_4$ or $NaCNBH_3$. Alternatively, the hydrazone linkage is maintained to provide a prodrug-like conjugate. In this embodiment, the aqueous plasma environment allows hydrolysis of the hydrazone bond, regenerating the starting glycoproteins in vivo.

The process of the present invention includes preparing or providing the activated polymer and thereafter reacting it with a Factor IX protein having at least one oxidized carbohydrate moiety. The carbohydrate moieties can be oxidized by reacting the glycoprotein in aqueous solution with sodium periodate or enzymatically using galactose oxidase or combination of neuraminidase and galactose oxidase as disclosed by Solomon et al., *J. Chromatography*, 510, 321–9 (1990). The reaction is preferably run at temperatures of about 0°–10 C.° when reacting with sodium periodate or at about room temperature when the carbohydrate moieties are being oxidized enzymatically. The reaction medium is preferably buffered, depending upon the requirements of the glycoprotein. The oxidized glycoprotein is then recovered and separated from the excess periodate by column chromatography, dialysis, ultrafiltration or the like.

The reaction is carried out in a buffer such as 0.1M phosphate buffer at a pH of from about 5.0 to about 8.0. The F.IX having at least one oxidized carbohydrate moiety is reacted with an appropriate amount of the activated polymer, which is typically present in a molar excess relative to the F.IX. The polymeric excess preferably ranges from about 10 to about 100 molar ratio excess of the polymer of the F.IX. The reaction is carried out at temperatures from about 0° to about 37° C. over time periods ranging from a few minutes to as long as 24 hours. Temperatures from about 10° to about 25° C. are preferred and time periods of about 2 hours are sufficient to carry out the conjugation reaction.

In addition to or as an alternative to the above-described carbohydrate-directed modification, further polymeric modification is possible. For example, epsilon amino lysine groups can be modified with appropriately functionalized polymers or additional active moieties. See, for example, U.S. Pat. No. 4,179,337 and 5,122,614, which are incorporated by reference herein.

Following the conjugation reaction, the desired product is recovered using known techniques and purified using column chromatography or similar apparatus, if necessary. Depending upon the reaction conditions, the conjugates have from about 1 to about 10 polymeric chains attached to the glycoprotein. By controlling the molar excess of the oxidant and the polymer with respect to the glycoprotein, the artisan can tailor the number of polymeric chains attached. Conjugates containing from about 3 to about 8 polymeric chains are preferred, while conjugates containing from about 3 to about 5 polymeric chains are most preferred.

Another aspect of the present invention provides methods of treating hemophilia B. For purposes of the present invention, treating includes prevention and/or prophylaxis. The methods include administering, in a pharmaceutically acceptable vehicle, such as a parenteral solution, an effective amount of the compositions described herein to alleviate clotting deficiencies. Those of ordinary skill in the art will realize that the amount of the conjugate used in the method of the present invention will vary somewhat from patient to patient, however, conjugates capable of delivering from about 0.1 IU/kg to about 10 IU/kg per administration or an amount sufficient to achieve or maintain a level of between 0.2 IU/ml–5 IU/ml blood are preferred. The optimal dosing of the conjugate can be determined from clinical experience. Essentially, the objective of treatment is to normalize serum F.IX levels and provide normal clotting times for Hemophilia B patients.

Modification of Factor IX with Polyethylene Glycol (PEG)

EXAMPLE 1

Purified human pooled Factor IX (3.7 mg/ml) obtained from the American Red Cross was dialyzed overnight against 50 mM sodium phosphate pH 6.25, 100mM NaCl. To 2.5 mg. of Factor IX ($4.4 \times 10^{-5}$ mmol) was added a 300 fold molar excess of $NaIO_4$ (69µl of a 40 mg/ml solution) to oxidize the carbohydrate moieties. The reaction mixture which was left to incubate on ice for one hour in the dark. A 200 fold molar excess of PEG-carbazate was then added and the reaction allowed to proceed overnight at 4° C. The resulting solution was then dialyzed against 50 mM sodium phosphate pH 7.0, 100 mM NaCl using a Pierce microdialyzer system. The activity of the PEG modified Factor IX, oxidized Factor IX and an unmodified control were determined in the presence of FIX- deficient plasma using a Dade chromogenic assay kit, available from Baxter, Inc., Deerfield, Ill. and are set forth below.

| SAMPLE | SPECIFIC ACTIVITY (U/MG) |
|---|---|
| FIX Control | 134 |
| Oxidized FIX | 120 |
| PEG-FIX | 111 |

EXAMPLE 2

Purified Factor IX (3.7 mg/ml) obtained from the American Red Cross was desalted over a PD-10 column (Pharmacia) into 50 mM sodium citrate pH 5.5, 150 mM NaCl. Carbohydrate residues were oxidized by the addition of $NaIO_4$ to 5 mM and incubated on ice for 20 min. in the dark. Sucrose was added to 10 mM to quench the reaction and the entire mixture was desalted as described above. The oxidized Factor IX was then incubated with a 100 fold excess of PEG-hydrazide for 2 hr. at room temperature. The resulting hydrazone was chilled on ice for 10 min. then reduced to the corresponding hydrazide by treating with 5 mM $NaCNBH_4$ at 4° C. overnight. The PEG-Factor IX was purified by GPC-HPLC using a Showdex KB804 column eluted with 50 mM histidine pH 6.5, 5 mM $CaCl_2$, 100 mM NaCl. The purified sample was concentrated and aliquots were stored at either 4° C., -70° C. or lyophilized. The specific activities were determined in the presence of Factor IX deficient plasma using a Dade Factor IX chromogenic assay kit available from Baxter, Inc., Deerfield, Ill. and in a one stage APTT clotting assay.

| | SPECIFIC ACTIVITY (U/mg) | |
|---|---|---|
| SAMPLE | Chromogenic | Clotting |
| FIX Control | 93 | 197 |
| PEG-F.IX (4° C.) | 123 | 16 |
| PEG-F.IX (-70° C.) | 168 | 10 |
| PEG-F.IX (Lyoph) | 206 | 51 |

EXAMPLE 3

American Red Cross Factor IX (18.5 mg, 3.7 mg/ml) was desalted over a 30 ml Sephadex G-25M column into 50 mM citrate pH 5.5, 150 mM NaCl. The protein was treated with 5 mM $NaIO_4$ for 20 min at 4° C. in the dark. The reaction was quenched by the addition of sucrose to 10 mM and the mixture was desalted as described above. A 100-fold molar excess of PEG-Carbazate was added to the oxidized protein and incubated at room temperature for 2 hr. After cooling on ice for 10 min. $NaCNBH_4$ was added to 5 mM and the reaction mixture was incubated on ice for 2 hr. The PEG-Factor IX was purified by GPC-HPLC using a Showdex KB804 column eluted with 50 mM histidine pH 6.5, 5 mM $CaCl_2$, 100 mM NaCl. Activities were determined in the presence of Factor IX deficient plasma using a Dade chromogenic assay kit and in a one stage APTT clotting assay.

| | SPECIFIC ACTIVITY (U/mg) | |
|---|---|---|
| SAMPLE | Chromogenic | Clotting |
| F.IX control | 106 | 288 |
| PEG-F.IX | 45 | 69 |

EXAMPLE 4

1 ml of purified Factor IX (4.75 mg/ml) obtained from Alpha Therapeutics, Los Angeles, Calif. (Lot# 52018), was desalted on a PD-10 column equilibrated with 100 mM NaAc pH 5.5, 150 mM NaCl. Fractions containing protein were pooled and 0.5M $NaIO_4$ was then added to a final concentration of 5 mM. The oxidation proceeded on ice for 20 minutes. The reaction was quenched by the addition of 0.1M sucrose to a final concentration of 10 mM and was allowed to sit on ice for 5 minutes. Excess periodate and sucrose were removed by desalting on a PD-10 column as described above, A 100 fold excess PEG-Hydrazide was added, and the reaction proceeded for 2 hours at room temperature. After cooling on ice, 0.5M $NaCNBH_4$ was added to a final concentration of 5 mM and the mixture was kept refrigerated overnight. Excess PEG and $NaCNBH_4$ were removed by GPC-HPLC using a Showdex column equilibrated with 0.1M sodium phosphate pH 7.5. SDS-PAGE of the purified material revealed a molecular weight shift to around 150-225 kD with no trace of native F.IX.

The sample was concentrated to approximately 1 ml using a centricon 30 centrifugal concentrator. Protein determination was performed using a Pierce BCA protein assay kit and Factor IX activity was determined using a Dade Factor IX chromogenic assay kit in the presence of Factor IX deficient plasma. The PEG-F.IX was calculated to retain 85% activity.

EXAMPLE 5

Purified Factor IX (49.4 mg) obtained for Alpha Therapeutics Corporation, Los Angeles, Calif. was buffer exchanged using a 30K NMWL cutoff miniultrasette tangential flow apparatus (Filtron) into 50 mM citrate, pH 5.5 150 mM NaCl. The volume was adjusted to approximately 30 ml and the protein was treated with 5 mM $NaIO_4$ for 20 min., on ice, in the dark. The oxidation reaction was quenched with 10 mM sucrose and the mixture was buffer exchanged as described above. A 100-fold molar excess of PEG-carbazate was added and the coupling reaction was incubated at room temperature for 2 hr. After cooling on ice for 10 min., $NaCNBH_4$ was added to 5 mM and the reaction mixture was incubated at 4° C. overnight. The reaction mixture was desalted using a miniultrasette apparatus with 50 mM histidine, pH 6.2, 5 mM $CaCl_2$, 100 mM NaCl with 10 mg/ml glycine. The sample was aliquoted and stored at either 4° C., -70° C. or lyophilized. SDS-PAGE revealed an increased and broad molecular weight distribution but no sign of contaminating native protein. Specific activities were determined in the presence of Factor IX deficient plasma using a Dade chromogenic assay kit.

| SAMPLE | SPECIFIC ACTIVITY (U/mg) |
| --- | --- |
| Native Factor IX | 47 |
| PEG-F.IX (4° C.) | 128 |
| PEG-F.IX (−70° C.) | 146 |
| PEG-F.IX (Lyoph) | 115 |

The various embodiments of the present invention, therefore, provide conjugates which retain significant levels of Factor IX activity while having less of a tendency to cause the formation of inhibitor antibodies.

We claim:

1. A biologically active conjugate comprising a first substance having Factor IX activity bound to a substantially non-antigenic polymeric substance by a linkage containing a hydrazide or hydrazone functional group.

2. The conjugate of claim 1 wherein said first substance comprises Factor IX.

3. The conjugate of claim 2 wherein said Factor IX is of mammalian origin.

4. The conjugate of claim 3 wherein said origin of said mammalian Factor IX is selected from the group consisting of human, porcine, bovine, and mixtures thereof.

5. The conjugate of claim 1 wherein said polymeric substance comprises a poly(alkylene oxide).

6. The conjugate of claim 5 wherein said polymeric substance comprises an alpha-substituted polyalkylene oxide derivative.

7. The conjugate of claim 5 wherein said polymeric substance is selected from the group consisting of polyethylene glycol homopolymers, polypropylene glycol homopolymers, alkyl-capped polyethylene oxides, bis-polyethylene oxides, copolymers of poly(alkylene oxides) and block copolymers of poly(alkylene oxides).

8. The conjugate of claim 5 wherein said polymeric substance comprises poly(ethylene glycol).

9. The conjugate of claim 1 wherein said substantially non-antigenic polymeric substance is selected from the group consisting of polyvinyl pyrrolidone, dextran, complex carbohydrates, starches and mixtures thereof.

* * * * *